(12) United States Patent
Takamori et al.

(10) Patent No.: US 7,852,080 B2
(45) Date of Patent: Dec. 14, 2010

(54) MRI APPARATUS INCLUDING A LIGHTING UNIT

(75) Inventors: Hiromitsu Takamori, Otawara (JP); Ayumi Katsunuma, Otawara (JP); Kazuhiko Tsujita, Otawara (JP); Souhei Fukunishi, Nasushiobara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 11/944,539

(22) Filed: Nov. 23, 2007

(65) Prior Publication Data

US 2008/0204017 A1 Aug. 28, 2008

(30) Foreign Application Priority Data

Nov. 24, 2006 (JP) .............................. 2006-316976

(51) Int. Cl.
*G01V 3/00* (2006.01)
(52) U.S. Cl. ..................................... 324/318; 324/307
(58) Field of Classification Search ......... 324/300–322; 600/410–435
See application file for complete search history.

(56) References Cited

U.S. PATENT DOCUMENTS

| | | | | | |
|---|---|---|---|---|---|
| 4,629,989 | A | * | 12/1986 | Riehl et al. | 324/318 |
| 5,204,629 | A | * | 4/1993 | Ueyama | 324/318 |
| 5,398,686 | A | * | 3/1995 | Inoue et al. | 600/415 |
| 5,548,215 | A |   | 8/1996 | Kohno et al. | |
| 5,577,095 | A | * | 11/1996 | Kobayashi | 378/206 |
| 5,682,891 | A |   | 11/1997 | Sonoki et al. | |
| 6,041,249 | A | * | 3/2000 | Regn | 600/429 |
| 6,490,477 | B1 | * | 12/2002 | Zylka et al. | 600/429 |
| 6,721,588 | B2 | * | 4/2004 | Drobnitzky | 600/410 |
| 6,744,251 | B2 | * | 6/2004 | Taniguchi et al. | 324/318 |
| 6,759,847 | B2 | * | 7/2004 | Brinker et al. | 324/309 |
| 7,034,535 | B2 | * | 4/2006 | Yamagata | 324/318 |
| 7,123,008 | B1 | * | 10/2006 | Damadian et al. | 324/309 |
| 7,123,758 | B2 | * | 10/2006 | Jeung et al. | 382/128 |
| 7,191,100 | B2 | * | 3/2007 | Mostafavi | 702/189 |
| 7,204,254 | B2 | * | 4/2007 | Riaziat et al. | 128/897 |

(Continued)

FOREIGN PATENT DOCUMENTS

CN 1104883 A 7/1995

(Continued)

*Primary Examiner*—Melissa J Koval
*Assistant Examiner*—Dixomara Vargas
(74) *Attorney, Agent, or Firm*—Oblon, Spivak, McClelland, Maier & Neustadt, L.L.P.

(57) ABSTRACT

An MRI apparatus has a gantry, a bed and a lighting unit collective including a plurality of lighting units. The gantry accommodates a static field magnet configured to generate a static field, a gradient coil configured to generate a gradient magnetic field, and an RF coil configured to transmit or receive an RF pulse as well as having an opening into which a person is inserted. The bed has a removable table-top for an inside and an outside of the opening. The lighting unit group is disposed at at least one of an inside position of the opening and an outside position from which an inside of the opening can be lighted so that the lighting units can carry out lighting such that an amount of emitting light increases bit by bit from a bedside to a counter bedside opposite to the bedside across the opening.

17 Claims, 9 Drawing Sheets

U.S. PATENT DOCUMENTS

| | | | |
|---|---|---|---|
| 7,272,207 B1 * | 9/2007 | Aufrichtig et al. | 378/116 |
| 7,280,635 B2 * | 10/2007 | Toth | 378/108 |
| 7,331,698 B2 * | 2/2008 | Gosswein et al. | 362/572 |
| 2005/0004444 A1 | 1/2005 | Boninger et al. | |

FOREIGN PATENT DOCUMENTS

| | | |
|---|---|---|
| CN | 1116079 A | 2/1996 |
| CN | 1550207 A | 12/2004 |
| CN | 1695549 A | 11/2005 |
| JP | 63-145643 | 6/1988 |
| JP | 2-98003 | 4/1990 |
| JP | 6-327646 | 11/1994 |
| JP | 2004-89621 | 3/2004 |

\* cited by examiner

FIG. 1

| RESPECTIVE PROCESSES IN FOOT EXAMINATION | LIGHTING PATTERN | | | |
|---|---|---|---|---|
| | INSIDE OF OPENING-BEDSIDE LIGHTING UNIT 16 | INSIDE OF OPENING-LATERAL LIGHTING UNIT 17 | INSIDE OF OPENING-COUNTER BEDSIDE LIGHTING UNIT 18 | COUNTER BEDSIDE LIGHTING UNIT 19 |
| FIRST PROCESS | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION |
| SECOND PROCESS | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION |
| THIRD PROCESS | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION |
| FOURTH PROCESS | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION | COLOR OF EMISSION / AMOUNT OF EMITTING LIGHT / MANNER OF EMISSION |

FIG. 2

| RESPECTIVE PROCESSES IN HEAD EXAMINATION | LIGHTING PATTERN | | | | | | | | | | | |
|---|---|---|---|---|---|---|---|---|---|---|---|---|
| | INSIDE OF OPENING-BEDSIDE LIGHTING UNIT 16 | | | INSIDE OF OPENING-LATERAL LIGHTING UNIT 17 | | | INSIDE OF OPENING-COUNTER BEDSIDE LIGHTING UNIT 18 | | | COUNTER BEDSIDE LIGHTING UNIT 19 | | |
| FIRST PROCESS | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION |
| SECOND PROCESS | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION |
| THIRD PROCESS | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION |
| FOURTH PROCESS | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION | COLOR OF EMISSION | AMOUNT OF EMITTING LIGHT | MANNER OF EMISSION |

| RESPECTIVE PROCESSES IN FOOT EXAMINATION | | LIGHTING PATTERN | | | |
|---|---|---|---|---|---|
| | | INSIDE OF OPENING-BEDSIDE LIGHTING UNIT 16 | INSIDE OF OPENING-LATERAL LIGHTING UNIT 17 | INSIDE OF OPENING-COUNTER BEDSIDE LIGHTING UNIT 18 | COUNTER BEDSIDE LIGHTING UNIT 19 |
| FIRST PROCESS | LIGHTING PATTERN L1 | ○ | ○ | ○ | ○ |
| SECOND PROCESS | LIGHTING PATTERN L1 | ○ | ○ | ○ | ○ |
| | LIGHTING PATTERN L2 | ○ (LARGE) | ○ (SMALL) | ○ (SMALL) | ○ (SMALL) |
| | LIGHTING PATTERN L3 | ○ | ○ | × | × |
| | LIGHTING PATTERN L4 | ○ | ○ | ○ | × |
| THIRD PROCESS | LIGHTING PATTERN L5 | ○ (SMALL) | ○ (MEDIUM) | ○ (LARGE) | ○ (LARGE) |
| | LIGHTING PATTERN L6 | ○ (SMALL) | ○ (MEDIUM) | ○ (LARGE) | ○ (MEDIUM) |
| | LIGHTING PATTERN L7 | ○ (LARGE) | ○ (SMALL) | ○ (LARGE) | ○ (SMALL) |
| | LIGHTING PATTERN L8 | ○ (SMALL) | ○ | ○ | ○ (SMALL) |
| FOURTH PROCESS | LIGHTING PATTERN L9 | × | ○ | ○ | ○ |
| | LIGHTING PATTERN L10 | × | ○ | × | ○ |

MRI APPARATUS INCLUDING A LIGHTING UNIT

BACKGROUND OF THE INVENTION

1. Field of the Invention

The present invention relates to a magnetic resonance imaging (MRI) apparatus for obtaining the anatomical information and biochemical information of a person making use of a magnetic resonance phenomenon.

2. Description of the Related Art

There is known, as the MRI apparatus, an apparatus for displaying images as tomographic images of a distribution of nuclear spin density and a distribution of relaxation time in a desired examination part of the person by measuring signals sent from a measurement target. Since an opening (space) formed to a gantry of the MRI apparatus, through which the person is inserted, has only a size that permits the person to enter thereinto, there is a possibility that a feeling of uneasiness may be applied to the person who is subjected to an examination from that time.

To cope with this problem, the MRI apparatus is provided with a lighting unit for lighting the gantry (for example, "Japanese Patent Application Publication (Laid-open: KOKAI) No. JP-A 2006-110043").

However, the lighting unit, disclosed in the "Japanese Patent Application Publication No. JP-A 2006-110043", cannot sufficiently eliminate the feeling of uneasiness of the person before the person is inserted into the opening as well as cannot sufficiently provide the person with a comfortable occupant feeling when the person is inserted into the opening, although the lighting unit can light the opening and the gantry brightly.

SUMMARY OF THE INVENTION

The present invention has taken into consideration the above-described problems, and it is an object of the present invention to provide the MRI apparatus which can improve a sense of safety and a comfort that the person feels.

To solve the above-described problems, the present invention provides an MRI apparatus, comprising: a gantry accommodating a static field magnet configured to generate a static field, a gradient coil configured to generate a gradient magnetic field, and an RF coil configured to transmit or receive an RF pulse as well as having an opening into which a person is inserted; a bed having a removable table-top for an inside and an outside of the opening; and a lighting unit collective, including a plurality of lighting units, disposed at at least one of an inside position of the opening and an outside position from which an inside of the opening can be lighted so that the lighting units can carry out lighting such that an amount of emitting light increases bit by bit from a bedside to a counter bedside opposite to the bedside across the opening.

To solve the above-described problems, the present invention provides an MRI apparatus, comprising: a gantry accommodating a static field magnet configured to generate a static field, a gradient coil configured to generate a gradient magnetic field, and an RF coil configured to transmit or receive an RF pulse as well as having an opening into which a person is inserted; a bed having a removable table-top for an inside and an outside of the opening; and a lighting unit disposed at an inside position of the opening on a bedside for carrying out lighting to an inside of the opening on the bedside or to a cover of the RF coil.

To solve the above-described problems, the present invention provides an MRI apparatus, comprising: a gantry accommodating a static field magnet configured to generate a static field, a gradient coil configured to generate a gradient magnetic field, and an RF coil configured to transmit or receive an RF pulse as well as having an opening into which a person is inserted; a bed having a removable table-top for an inside and an outside of the opening; and a photoconductor disposed at an inside position of the opening for transmitting light from a light source extending in the longer direction of the table-top.

To solve the above-described problems, the present invention provides an MRI apparatus, comprising: a gantry accommodating a static field magnet configured to generate a static field, a gradient coil configured to generate a gradient magnetic field, and an RF configured to for transmit or receive an RF pulse as well as having an opening into which a person is inserted; a bed having a removable table-top for an inside and an outside of the opening; a first lighting unit disposed at an inside position of the opening on a counter bedside opposite to a bedside across the opening or to an outside position from which an inside of the opening can be lighted on the counter bedside for carrying out lighting to the inside of the opening; and a second the lighting unit disposed at an inside position of the opening on the bedside for carrying out lighting to a shade formed by a step of the opening by the lighting from the first lighting unit.

DETAILED DESCRIPTION OF PREFERABLE EMBODIMENT

An embodiment of an MRI apparatus according to the present invention will be explained below referring to FIG. 1 to FIG. 11.

Figure 1:
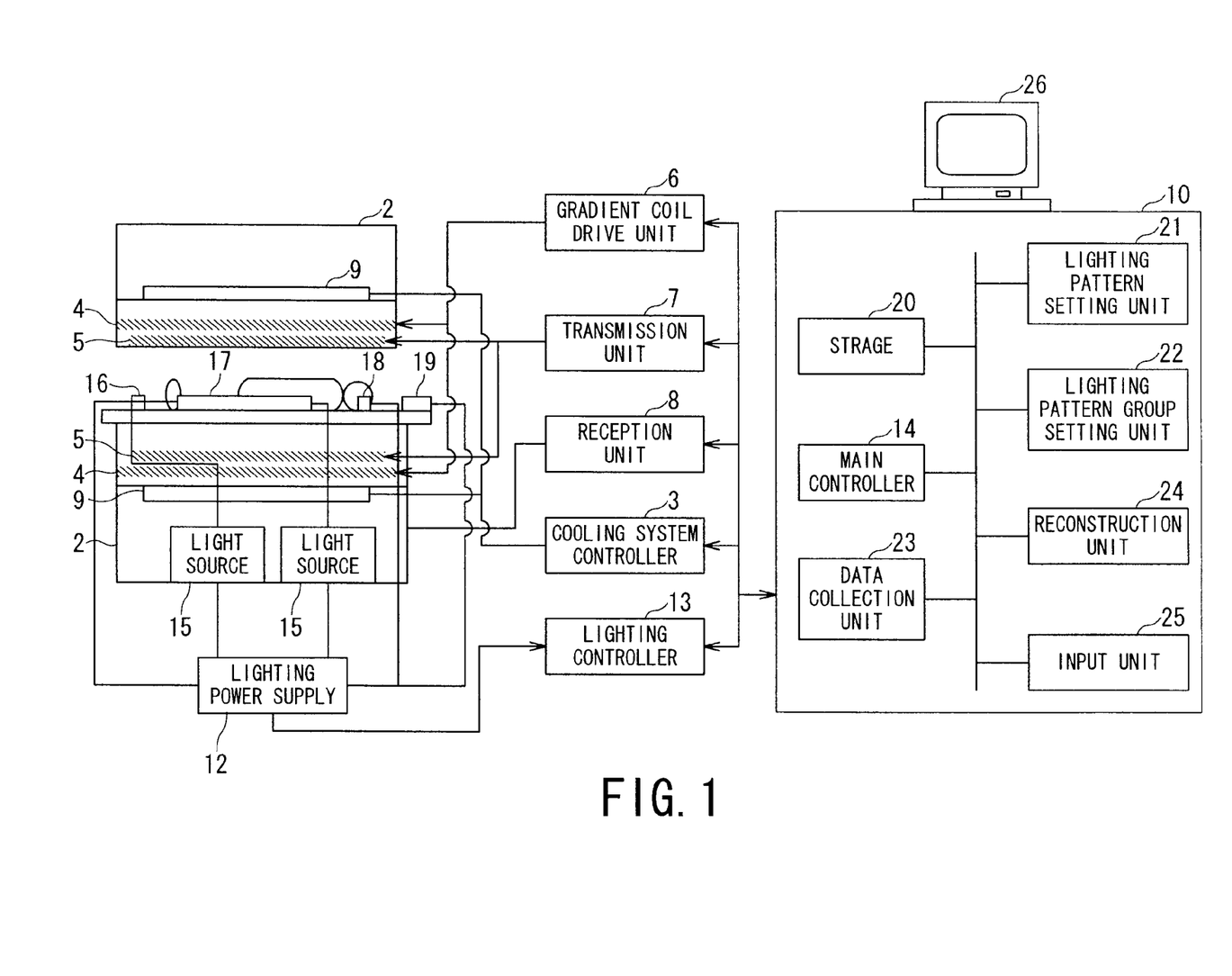
FIG. 1 is a view showing the arrangement of the MRI apparatus of the embodiment.

FIG. 1 is a view showing the arrangement of the MRI apparatus of the embodiment.

As shown in FIG. 1, the MRI apparatus of the embodiment includes a gantry and an opening having an insertion space through which a person is inserted into the gantry. The MRI apparatus further includes a static field magnet 2, a cooling system controller 3, a gradient coil 4, a radio frequency (RF) coil 5, a gradient coil drive unit 6, a transmission unit 7, a reception unit 8, a cooling unit 9, an arithmetic operation unit 10, a lighting power supply 12, a lighting controller 13, and a display unit 26. As used herein, the gantry includes the static field magnet 2 and a support unit for a table top of a patient bed, as well as associated supporting structures or housings.

The static field magnet 2 is a magnet for generating a static field and generates a uniform static field. A permanent magnet, a superconducting magnet, and the like, for example, are used as the static field magnet 2. The static field magnet 2 is cooled by a cooling system, for example, the cooling unit 9 and isolated from the outside by a vacuum layer and a cylindrical cabinet.

The cooling system controller 3 controls the cooling unit 9 for cooling the static field magnet 2, the gradient coil 4, the RF coil 5, and the like.

The gradient coil 4 is a magnetic field coil having an axis shorter than the static field magnet 2 and disposed at an inside of the static field magnet 2. The gradient coil 4 forms a gradient magnetic field having a distribution of linear gradient magnetic fields in three directions which are orthogonal with each other based on the pulse current supplied from the gradient coil drive unit 6. A site that is a cause of a signal generation (position) is specified by the gradient magnetic field generated by the gradient coil 4.

The RF coil 5 is a coil for generating an RF pulse for generating a magnetic resonance signal to an image pickup region. Further, when, for example, an abdominal area and the like are pick up, the RF coil 5 may be used as a reception coil. The RF coil 5 is, for example, a whole body coil (WB coil).

The gradient coil drive unit 6 generates a pulse current for forming a gradient magnetic field and supplies it to the gradient coil 4. Further, the gradient coil drive unit 6 controls the polarity of the gradient magnetic field by switching the direction of the pulse current supplied to the gradient coil 4 under the control of a main controller 14.

The transmission unit 7 includes an oscillation unit, a phase selection unit, a frequency conversion unit, an amplitude modulation unit, and an RF power amplifier (any of them is not shown) and transmits an RF pulse corresponding to a Larmor frequency to the RF coil 5. The magnetization of a predetermined atomic nucleus in an examination part of a person is placed in an excitation state by the radio frequency generated from the RF coil 5 according to the transmission.

The reception unit 8 includes an amplification unit, an intermediate frequency conversion unit, a phase detection unit, a filter, and an analog to digital (A/D) converter (any of them is not shown) and subjects the respective magnetic resonance signals (RF signals) received from respective receivers to predetermined signal processing, individually. That is, the reception unit 8 applies amplification processing, intermediate frequency conversion processing making use of an oscillation frequency, phase detection processing, filter processing, and A/D conversion processing to the magnetic resonance signal discharged when the magnetized nuclear is relaxed from the excited state to a ground state.

The lighting power supply 12 outputs power to the light source 15 of respective lighting units 16-19 to be described later which are disposed at the opening into which the person is inserted.

The lighting controller 13 controls the power output to the lighting power supply 12 in response to an instruction from the main controller 14 and adjustments the contents of lighting of the respective lighting unit. Here, the contents of lighting show at least one of a color of emission, an amount of emitting light, and a manner of emission of the lighting unit. Note that the lighting power supply 12 may be disposed at the outside of the gantry so that the disturbance of a magnetic field and the influence to an image caused by the ON/OFF of the power supply and the like can be suppressed.

Further, the arithmetic operation unit 10 includes a storage 20, a main controller 14, a lighting pattern setting unit 21, a lighting pattern group setting unit 22, a data collection unit 23, a reconstruction unit 24, and an input unit 25.

The storage 20 stores the magnetic resonance signal data before a reconstruction processing, the magnetic resonance signal data after the reconstruction processing, and the like of each person obtained through the reception unit 8, the contents of lighting of the respective lighting unit, the lighting patterns set by the lighting pattern setting unit 21, and the lighting pattern group in one examination set by the lighting pattern group setting unit 22.

The lighting pattern setting unit 21 combines the contents of lighting of the respective lighting unit, and sets lighting patterns in a respective lighting unit collective including a plurality of lighting units.

The lighting pattern group setting unit 22 sets a lighting pattern group by combining the lighting patterns, set in the respective lighting unit collective by the lighting pattern setting unit 21, with respective processes in one examination.

Figure 2:
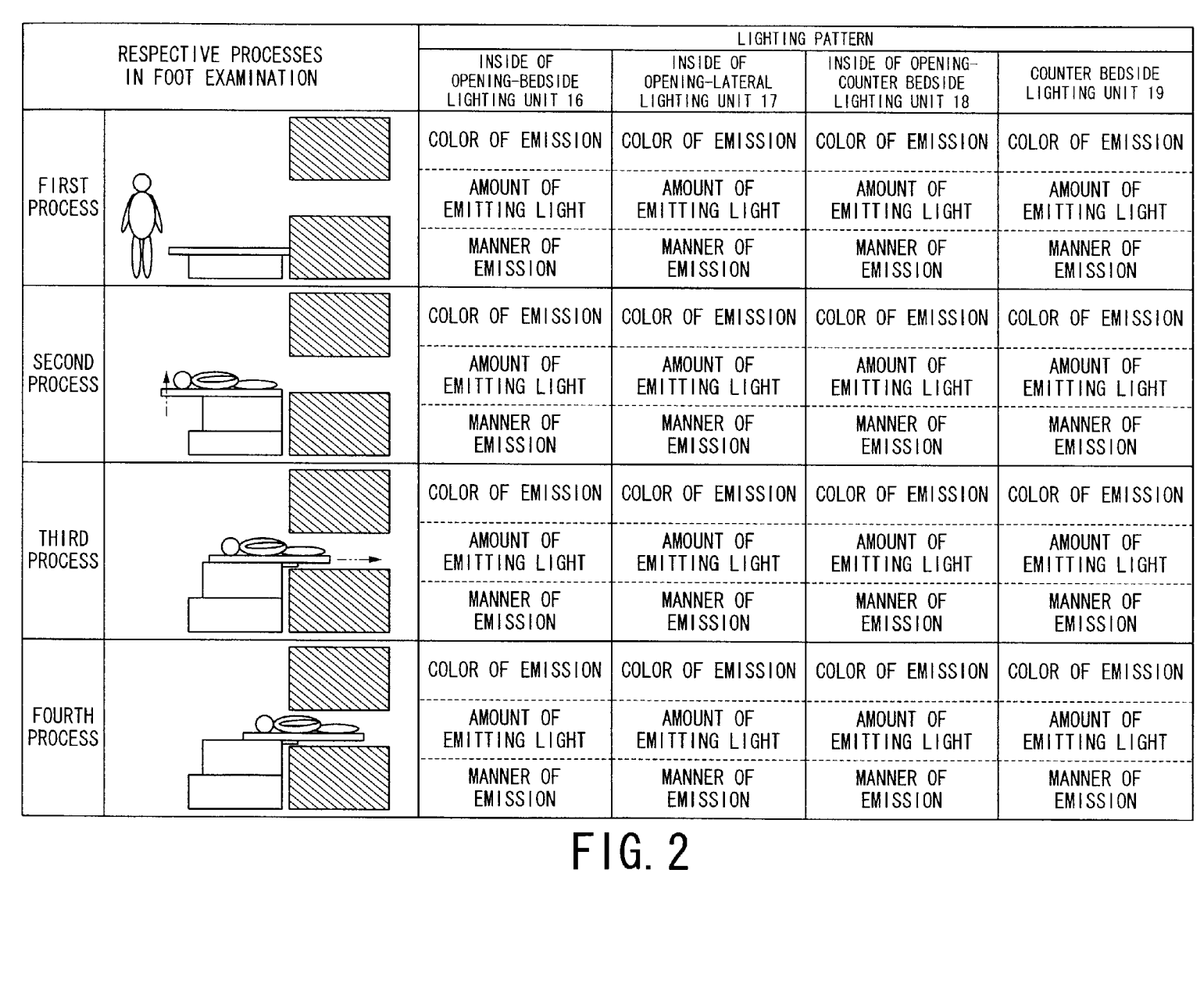
FIG. 2 is a view showing an outline of a lighting pattern group in a foot examination made by combining lighting patterns with respective processes in the foot examination using the MRI apparatus.
Figure 3:
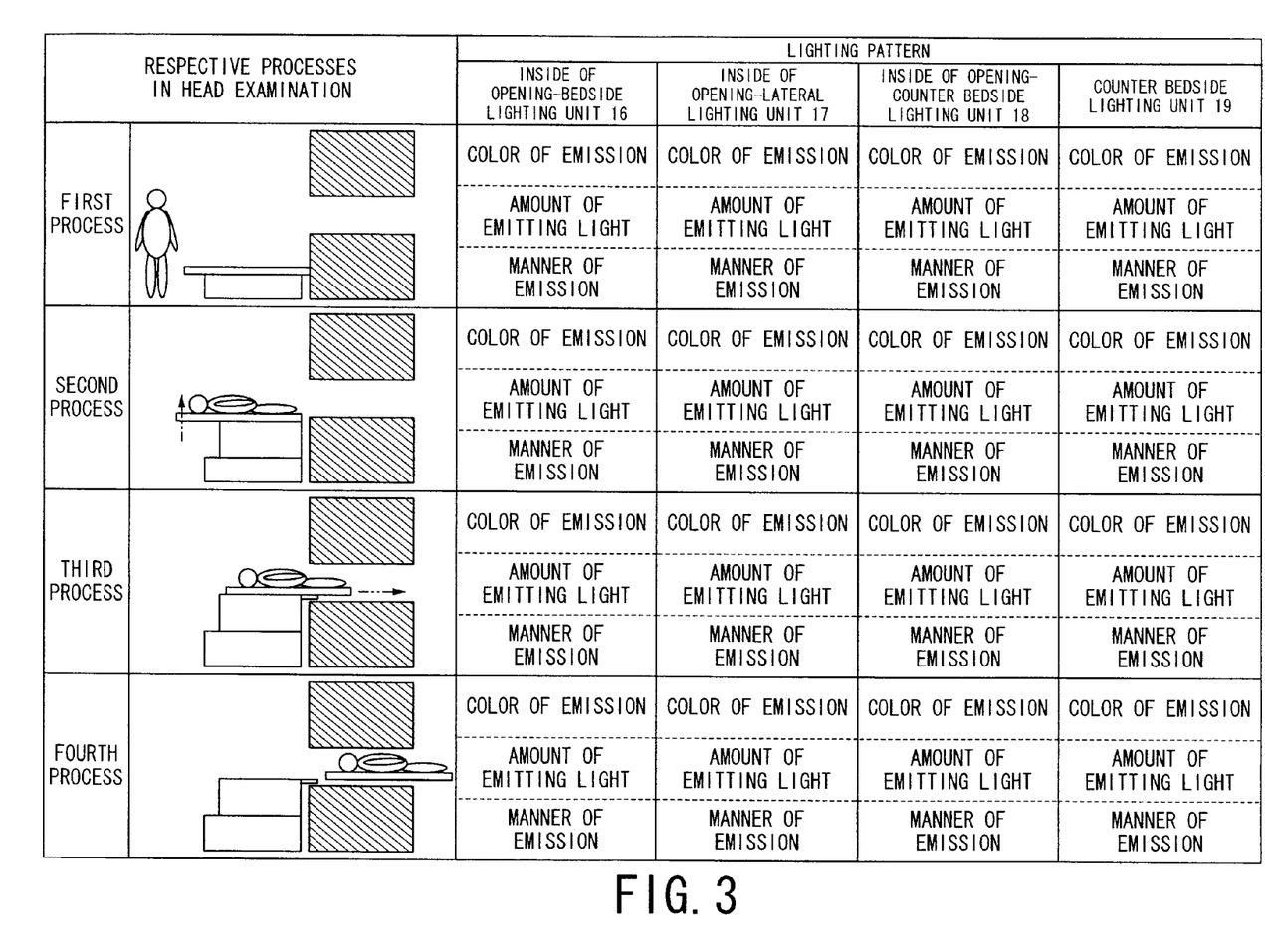
FIG. 3 is a view showing an outline of a lighting pattern group in a head examination made by combining lighting patterns with respective processes in the head examination using the MRI apparatus.

FIGS. 2 and 3 are views showing the outline of the lighting pattern group in one examination made by combining the lighting patterns with the respective processes in one examination using the MRI apparatus.

FIG. 2 shows the outline of a lighting pattern group in a foot examination formed by combining the lighting patterns set by the lighting pattern setting unit 21 with the respective processes when the foot examination using the MRI apparatus is divided into a process from the conveyance of the person into a room to the placement of him or her on a table-top (a first process), a process from the completion of the first process to the completion of rise of the table-top (a second process), a process of insertion of the table-top to an image pickup position (a third process), and a process during which the examination part in the person is being picked up (a fourth process). The lighting pattern group in the foot examination is arranged by combining the lighting patterns of the respective processes in the foot examination. Further, the lighting patterns of the respective processes of the foot examination process are arranged by combining the contents of lighting (the color of emission, the amount of emitting light, and the manner of emission).

FIG. 3 shows the outline of the lighting pattern group in a head examination formed by combining the lighting patterns set by the lighting pattern setting unit 21 with the respective processes, that is, the first process, the second process, the third process, and the fourth process.

Note that although the examination using the MRI apparatus is divided into the four processes in the embodiment as shown in FIGS. 2 and 3, 4, it is not limited to the four processes. Further, FIGS. 2 and 3 exemplify a method (foot first) for inserting the person into the opening from the foot side as the examination using the MRI apparatus, the MIR apparatus can be also applied to a method of inserting the person into the opening from a head side (head first).

Further, the data collection unit 23 shown in FIG. 1 collects the digital signals sampled by the reception unit 8.

The reconstruction unit 24 carries out post-processing, that is, the reconstruction processing such as Fourier transformation and the like and determines the spectrum data or the image data of a desired nuclear spin the examination part of the person.

The input unit 25 has input units (mouse, track ball, mode switch, keyboard, and the like) for fetching various instructions, commands, and information from an operator.

The main controller 14 has a central processing unit (CPU) as a not shown processor, a memory, and the like and statically or dynamically controls the system in its entirety as the center of control of the overall system. Note that the components 21-24 of the arithmetic operation unit 10 may be entirely or partly composed of software as the function of the main controller 14 or may be composed of circuits.

A display unit 26 is an output unit for displaying the spectrum data, the image data, and the like input from the arithmetic operation unit 10 through the main controller 14.

Further, the MRI apparatus has a bed (not shown) having a removable table-top, on which the person is placed, for an inside and an outside of the opening of the gantry 1. Note that, in the following description, the side where the bed is disposed is called a "bedside", and the side where the bed is not disposed is called a "counter bedside" when viewed from the gantry 1 in the inserting direction of the opening.

Figure 4:
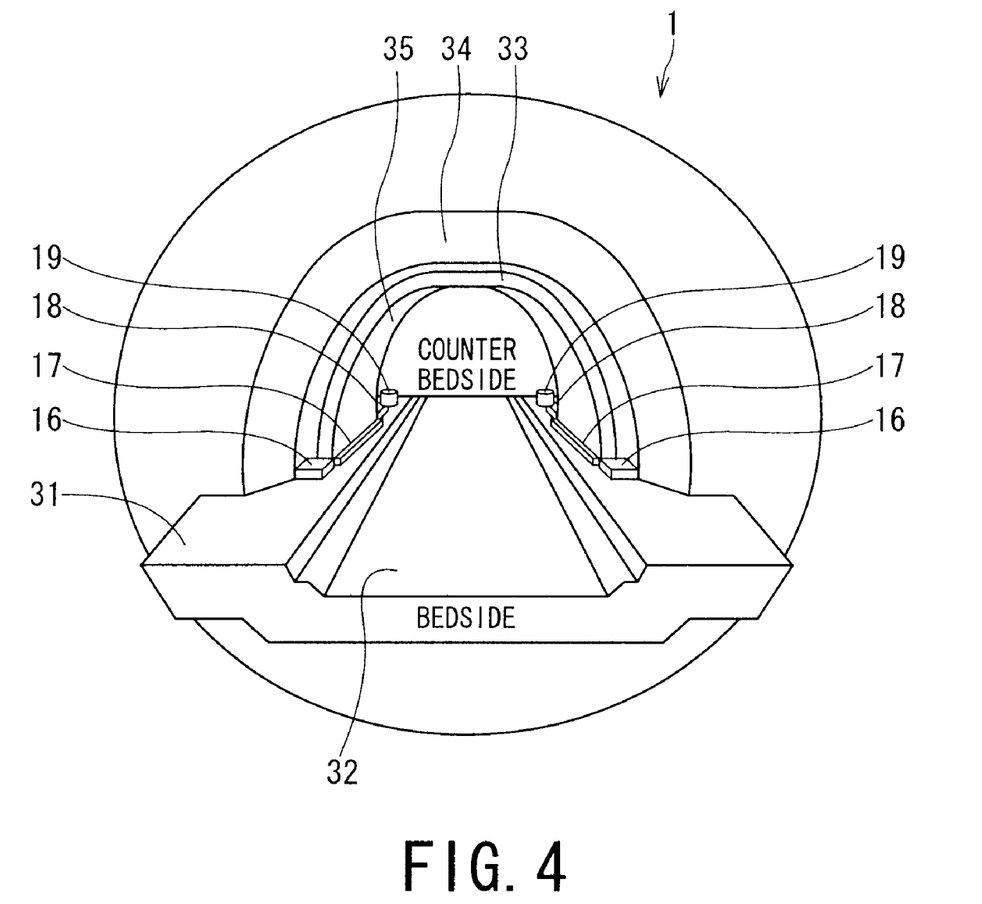
FIG. 4 is a perspective view of an opening constituting the MRI apparatus of the embodiment when viewed from a bedside.
Figure 5:
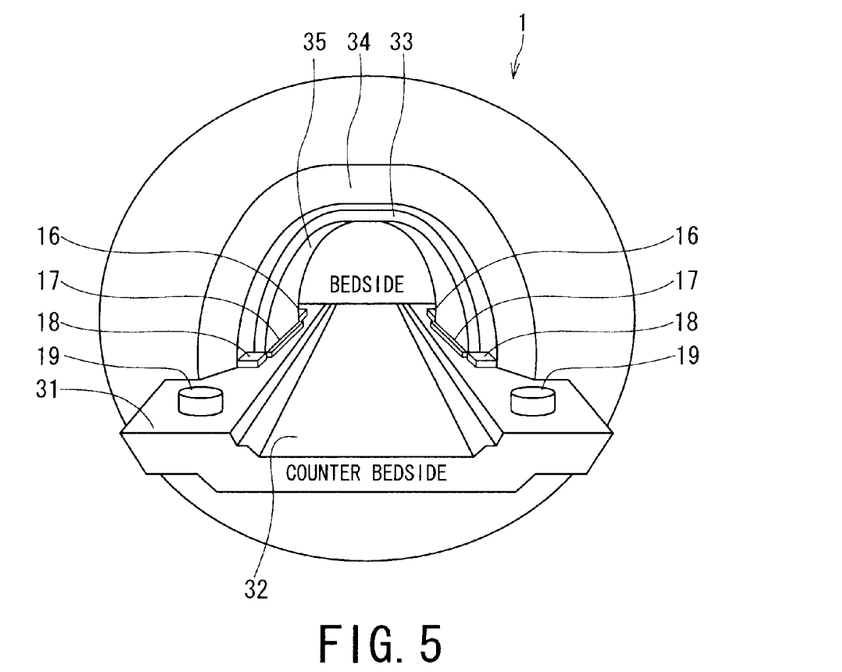
FIG. 5 is a perspective view of an opening constituting the MRI apparatus of the embodiment when viewed from a counter bedside.

Next, the lighting unit collective mounted on a support unit 31 will be explained in detail referring to FIG. 4 to FIG. 10. FIG. 4 is a perspective view of the opening constituting the MRI apparatus of the embodiment when viewed from the bedside. FIG. 5 is a perspective view of the opening constituting the MRI apparatus of the embodiment when viewed from the counter bedside.

First, as shown in FIG. 4 or FIG. 5, the MRI apparatus has an inside of opening-bedside lighting unit 16, an inside of opening-lateral lighting unit 17, and an inside of opening-counter bedside lighting unit 18 as the lighting unit, included in the lighting unit collective, from the bedside of the opening having the gantry 1 to the counter bedside. Further, as shown in FIG. 4 or FIG. 5, the MRI apparatus has a counter bedside lighting unit 19 as the lighting unit, included in the lighting unit collective, at a position from which it can light the inside of the opening from the outside thereof on the counter bedside.

The respective lighting units 16-19 are disposed at nearer to the wall of the opening than a rail 25 portion disposed on the support unit 31 into which the table-top is inserted. More preferably, the respective lighting units 16-19 are disposed on the support unit 31 approximately in alignment from the bedside to the counter bedside. Since the respective lighting units 16-19 are almost disposed in the same straight line, they are advantageous in that the concavo-convex states and the feeling of pressure of the person which are caused by lighting can be suppressed. It is explained below example that the respective lighting units 16-19 are almost disposed on the support unit 31 in the same straight line from the bedside to the counter bedside.

Further, more preferably, the respective lighting units 16-18 disposed at the opening are located to the lower half portion of the opening. When the respective lighting units 16-18, which are disposed at the lower half portion of the opening, are advantageous in that a large space into which a large insertion space can be secured as well as the influence of the electromagnetic wave of the RF coil 5 can be suppressed. The case, in which the respective lighting units 16-18 are disposed at the lower half region the opening, will be explained below as an example.

Here, the respective lighting units 16-18 (when they are almost disposed in the same straight line, the lighting unit 19 is also included), which are disposed at the opening, have a different relation of height to the top plate depending on the condition, such as a diameter of the opening into which the person is inserted, a size of the table-top and a height of the table-top. When the diameter of the opening is, for example, about 50-60 cm (centimeter), the respective lighting units 16-18 are generally disposed at below the table-top. On the other hand, when the diameter of the opening is larger than about 60 cm, they are generally disposed at above the table-top. The case, in which the respective lighting units 16-18 are disposed at above the table-top, will be explained as an example.

The inside of opening-bedside lighting unit 16 is disposed on the support unit 31 on the bedside in the opening. The inside of opening-bedside lighting unit 16 has a function for preventing shades made by the counter bedside lighting unit 19 and the like, that is, a function as auxiliary lighting of the counter bedside lighting unit 19 and the like. The inside of opening-bedside lighting unit 16 is preferably composed of an LED (light emitting diode) lamp for an emission of three colors (RGB). Note that the inside of opening-bedside lighting unit 16 may be composed of LED lamp for an emission of white color and the like.

Further, the inside of opening-bedside lighting unit 16 may be formed of an LED panel on which a plurality of LED lamps are disposed in a flat state in a predetermined shape. In this case, it is also possible to emit the plurality of LED lamps independently by providing them with a pattern under the control of the lighting controller 13 or to change the color of emission and the amount of emission in addition to that the plurality of LED lamps are emitted at the same time.

Figure 6:
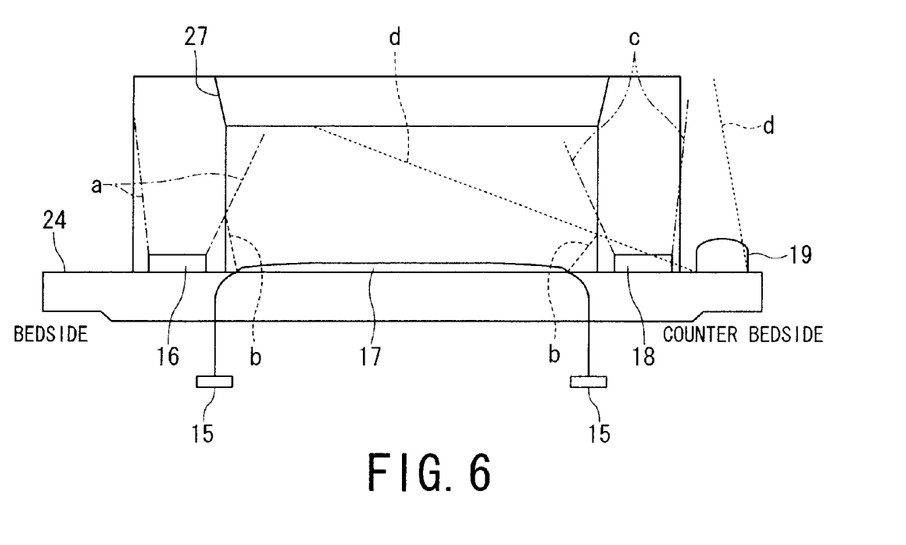
FIG. 6 is a view showing how an opening according to the embodiment is lighted when viewed from a lateral of an opening.

When the opening has no step, the inside of opening-bedside lighting unit 16 lights the vicinity of the entrance 34 of the opening, whereas when the opening has a step, they light the irregular portion of the step. Further, as shown in FIG. 4 or FIG. 5, when the RF coil 5 rises into the opening to increase the space thereof, the inside of opening-bedside lighting unit 16 lights the taper portion 33 thereof. For example, FIG. 6 is a view showing how the opening according to the embodiment is lighted when viewed from a lateral of the opening. The light in a lighting direction d, which shows the width of the lighting from the counter bedside lighting unit 19 of FIG. 6 can prevent the occurrence of a conventional shade (a shade S by lighting from a lighting unit 100 for a conventional MRI apparatus shown in FIG. 11) by canceling the shade, which is made to the taper portion 33 of a cover of the RF coil 5 by a lighting direction a which shows the width of the lighting carried out by the inside of opening-bedside lighting unit 16.

The inside of opening-lateral lighting unit 17 is disposed on the support unit 31 in the opening. The inside of opening-lateral lighting unit 17 transmits the light of the light source 15, which is located at a separate position as shown by FIG. 6, for example, below the gantry 1 and the like and extends in the longer direction of the table-top, to a light transmission member disposed along the lateral 35 in the opening so that the lateral 35 in the opening can be lighted as shown by a lighting direction b which shows the width of lighting. With this arrangement, lighting by gentle light can be established in contrast with the arrangement which a plurality of light sources are almost disposed in the same straight line.

Otherwise, the inside of opening-lateral lighting unit 17 is arranged such that it indirectly lights the wall of the opening by a line-shaped LED panel on which a plurality of LED lamps having constitution of the emission of three colors are disposed along the lateral 35 in the opening. In this case, it is also possible to emit the plurality of LED lamps independently by providing them with a pattern under the control of the lighting controller 13 or to change the color of emission and the amount thereof in addition to that the plurality of LED lamps are emitted at the same time.

As shown in FIG. 5, the inside of opening-counter bedside lighting unit 18 is disposed on the support unit 31 on the counter bedside in the opening. Further, the inside of opening-counter bedside lighting unit 18 lights the inside of the opening from the counter bedside and are disposed to light the inside of the opening as apparent from a lighting direction c that shows the width of lighting from the inside of opening-counter bedside lighting unit 18 of FIG. 6. The inside of opening-counter bedside lighting unit 18 is preferably composed of the LED lamp having constitution of the emission of three colors. Note that the inside of opening-counter bedside lighting unit 18 may be composed of an LED lamp having constitution of the emission of white color and the like.

Further, the inside of opening-counter bedside lighting unit 18 may be formed of the LED panel on which the LED lamps are disposed in the flat state in a predetermined shape. In this case, it is also possible to adjust the color of emission, the amount of emitting light, and the manner of emission under the control of the lighting controller 13.

As shown in FIG. 4 or FIG. 5, the counter bedside lighting unit 19 is disposed on the support unit 31 outside position of the opening on the counter bedside. Further, the counter bedside lighting unit 19 lights the inside of the opening from a side nearest to the counter bedside and are disposed to light the inside of the opening as apparent from a lighting direction d showing the width of lighting from the counter bedside lighting unit 19 of FIG. 6. However, the counter bedside lighting unit 19 may be disposed at positions, from which the inside of the opening can be lighted from the counter bedside, in an inspection room in which the MRI apparatus is installed in place of that they are disposed on the support unit 31. Further, the counter bedside lighting unit 19 is preferably composed of a fluorescent lamp or an incandescent lamp to increase a savanna effect to be described later. However, the counter bedside lighting unit 19 may be composed of the LED lamp and the like.

Further, it is also possible to control an amount of light of the counter bedside lighting unit 19 by the lighting controller 13.

When the lighting units 16-19 are not composed the LED lamp having constitution of the emission of three colors, a lighting color may be variously changed by putting covers to the lighting units 16-19. More particularly, it is preferable in this case to light the inside of the opening by putting warm color covers during an examination to provide the person with a feeling of easiness and a false feeling that the opening has a large size. Further, more particularly, when it is intended to provide the person with a false feeling that the opening has a long depth, covers employed a gradation are put to the inside of opening-lateral lighting unit 17 so that the inside of the opening is lighted brighter toward a deeper portion when viewed from the counter bedside, that is, from the side from which the person is inserted.

Note that the present invention is by no means limited to the above embodiment as it is and may be embodied by modifying the above components within the range which does not depart from the gist of the present invention. Further, various inventions may be made by appropriately combining the plurality of components disclosed the above embodiment. Some components may be deleted from all the components shown in the embodiment.

The embodiment is explained using the example including all of the lighting units 16-19 in the lighting unit collective. However, the embodiment may be embodied by the combination of only the an inside of opening-bedside lighting unit 16 and the counter bedside lighting unit 19, by only the inside of opening-lateral lighting unit 17, or by the combination of only the inside of opening-counter bedside lighting unit 18 and the counter bedside lighting unit 19, thereby an effect of improving the feeling of easiness and the comfortable sensation of the person can be improved.

Next, a specific example of lighting pattern groups in one examination, which are formed by combining the lighting patterns with the respective processes in one examination using the MRI apparatus, will be explained.

Figure 7:
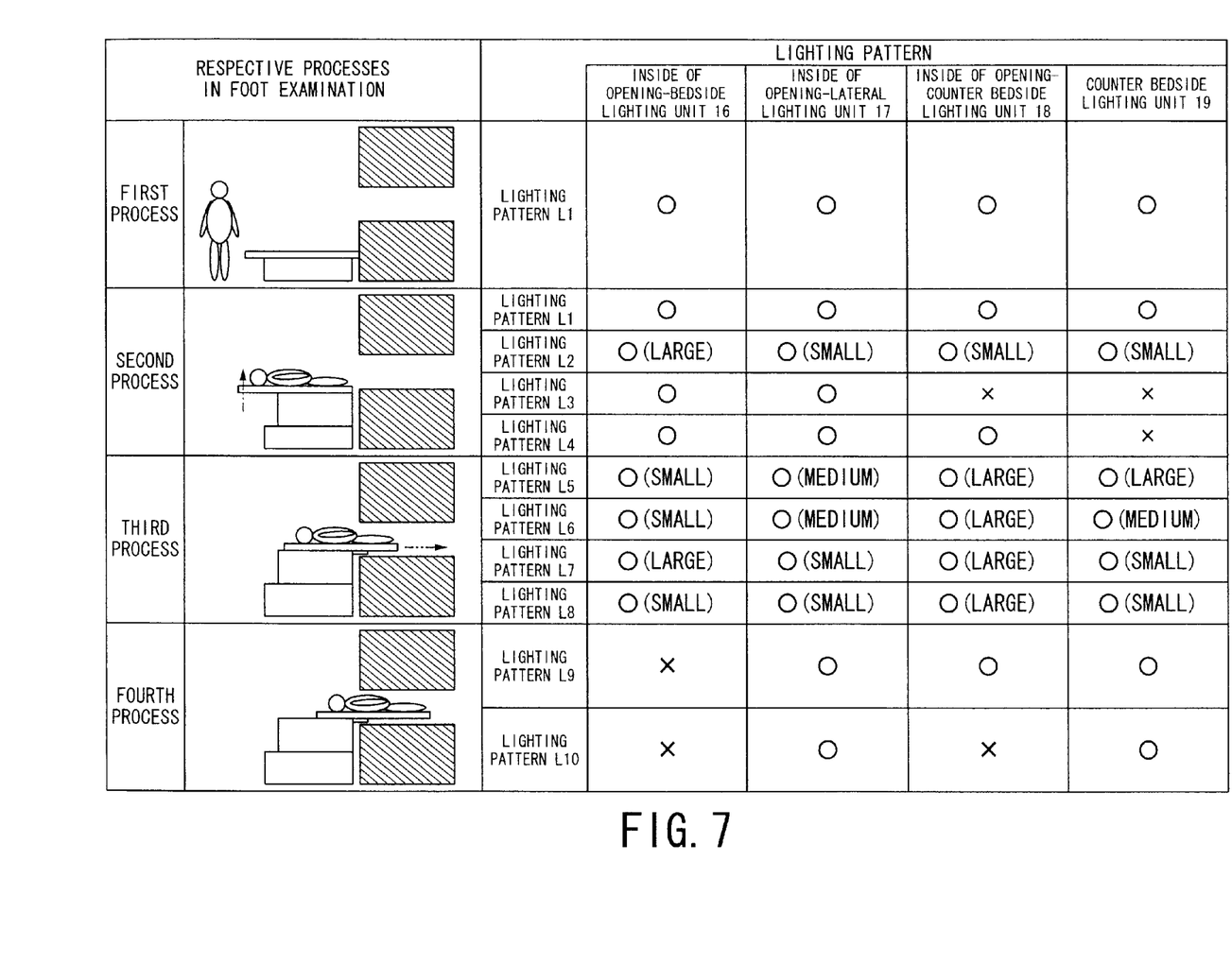
FIG. 7 is a view showing an example of a lighting pattern group in one examination made by combing lighting patterns with respective processes in one examination using the MRI apparatus.

FIG. 7 is a view showing an example of the lighting pattern group in one examination made by combing the lighting patterns with respective processes in one examination using the MRI apparatus.

FIG. 7 exemplifies the lighting pattern group in one examination which is arranged by combining the lighting patterns set by the lighting pattern setting unit 21 when the examination using the MRI apparatus is divided into the first process, the second process, the third process, and the fourth process as explained using FIG. 2. Note that FIG. 7 exemplifies a case of the foot examination and further exemplifies only the amount of emitting light as the contents of lighting.

[First Process]

It is preferable in the first process to make the overall opening bright. When, for example, the MRI apparatus includes all the lighting units 16-19, the first process causes all the lighting units 16-19 to emit (to be lit) according to a lighting pattern L1 as an example of the lighting pattern.

In the first process, when the person enters the room, the feeling of oppression and the awful feeling of the person to the MRI apparatus can be reduced by making the overall opening bright.

Note that the lighting patterns in the first process when the MRI apparatus includes all the lighting units 16-19 are not limited to the lighting pattern L1.

[Second Process]

In the second process, it is preferable to make the overall opening bright or the inside of the opening on the bedside bright as compared with the inside of the opening on the counter bedside. When, for example, the MRI apparatus includes all the lighting units 16-19, they are emitted according to the lighting pattern L1 to make the overall opening bright.

Further, when, for example, the MRI apparatus includes all the lighting units 16-19, the inside of opening-bedside lighting unit 16 is emitted in a large amount according to a lighting pattern L2 as an example of the lighting pattern to make the inside of the opening on the bedside bright as compared with the inside of the opening on the counter bedside, whereas the inside of opening-lateral lighting unit 17, the inside of opening-counter bedside lighting unit 18, and the counter bedside lighting unit 19 are emitted in a small amount.

Further, when, for example, the MRI apparatus includes all the lighting units 16-19, only the inside of opening-bedside lighting unit 16 and the inside of opening-lateral lighting unit 17 are emitted according to a lighting pattern L3 as an example of the lighting pattern to make the inside of the opening on the bedside bright as compared with the inside of the opening on the counter bedside.

Further, when, for example, the MRI apparatus includes all the lighting units 16-19, only the inside of opening-bedside lighting unit 16, the inside of opening-lateral lighting unit 17, and the inside of opening-counter bedside lighting unit 18 are emitted according to a lighting pattern L4 as an example of the lighting pattern to make the inside of the opening on the bedside bright as compared with the inside of the opening on the counter bedside.

Figure 11:
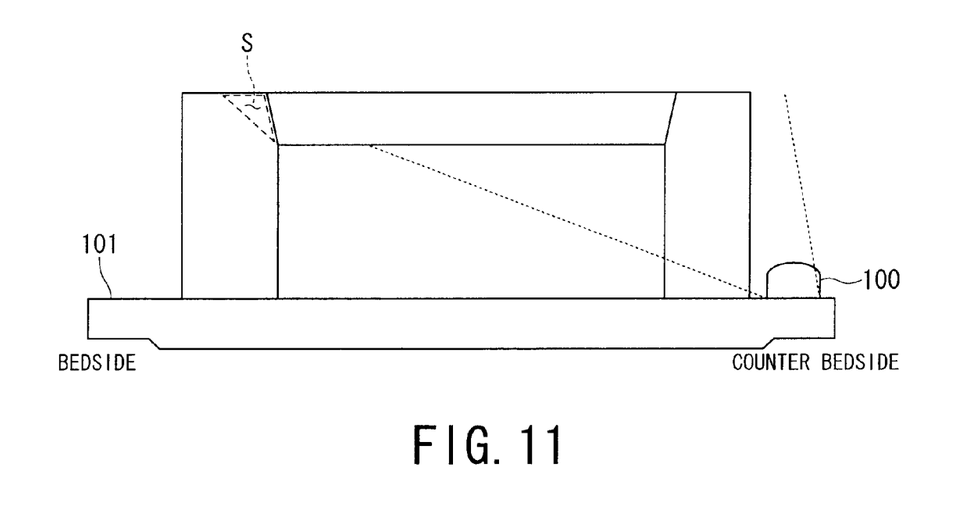
FIG. 11 is a perspective view showing placement of a lighting unit of a conventional MRI apparatus.

Since the overall opening is made bright in the second process, when the table-top, on which the person is placed, rises, the feeling of oppression and the awful feeling of the person to the MRI apparatus can be reduced. Further, since the inside of the opening on the bedside is made bright in comparison with the inside of the opening on the counter bedside in the second process, when the table-top, on which the person is placed, rises, the shade S as shown in FIG. 11 is not formed. Further, since the attention of the person is not directed to the inside of the opening on the counter bedside and can be directed to the inside of the opening on the bedside, the attention can be taken off from the depth of the opening. Further, since the counter bedside lighting unit 19 is not turned on in the second process by employing the lighting patterns L3 and L4, the shade S as shown in FIG. 11 is not formed.

Note that the lighting patterns in the second process when the MRI apparatus includes all the lighting units 16-19 are not limited to the lighting patterns L1-L4.

[Third Process]

In a third process, the inside of the opening on the counter bedside is preferably made bright in comparison with the inside of the opening on the bedside. When, for example, the MRI apparatus include all the lighting units 16-19, the inside of opening-bedside lighting unit 16, the inside of opening-lateral lighting unit 17, the inside of opening-counter bedside lighting unit 18, and the counter bedside lighting unit 19 are emitted according to a lighting pattern L5 as an example of the lighting pattern so that the amounts of emitting light increases bit by bit in this order.

Further, when for example, the MRI apparatus include all the lighting units 16-19, the inside of opening-counter bedside lighting unit 18 is emitted in a large amount, then the inside of opening-lateral lighting unit 17 and the counter bedside lighting unit 19 are emitted in a medium amount, and the inside of opening-bedside lighting unit 16 is emitted in a small amount according to a lighting pattern L6 as an example of the lighting pattern. Note that, in this case, the inside of opening-bedside lighting unit 16 may be turned off.

Further, when, for example, the MRI apparatus include all the lighting units 16-19, the inside of opening-bedside lighting unit 16 and the inside of opening-counter bedside lighting unit 18 are emitted in a large amount, and the inside of opening-lateral lighting unit 17 and the counter bedside lighting unit 19 are emitted in a small amount of emitting light according to a lighting pattern L7 as an example of the lighting pattern.

Further, when, for example, the MRI apparatus include all the lighting units 16-19, the inside of opening-counter bedside lighting unit 18 are emitted in a large amount, and the inside of opening-bedside lighting unit 16, the inside of opening-lateral lighting unit 17, and the counter bedside lighting unit 19 are emitted in a small amount according to a lighting pattern L8 as an example of the lighting pattern.

Since the inside of the opening on the counter bedside is made bright in comparison with the inside of the opening on the bedside in the third process, when the person is inserted, the savanna effect is made by making the inside of the opening on the counter bedside brighter than the inside of the opening on the bedside, thereby the person has a false feeling that the depth of the inside of the opening is shorter than an actual depth.

Further, the inside of opening-lateral lighting unit 17 is composed of a plurality of LED panels disposed in the straight line and the LED panels are caused to sequentially emit light to the opening on the bed side from the counter bedside of the opening according to the degree of insertion of the table-top into the opening. With this operation, the person can be made to have a false feeling that the space in the opening increases from the counter bedside to the bedside. Further, a visually distinct color may be used so that the person intensively turns the person's line of sight to the color.

Note that when the MRI apparatus include all the lighting units 16-19 in the third process, the lighting patterns are not limited to the lighting patterns L5-L8.

[Fourth Process]

In a fourth process, it is preferable to make the contrast of the inside of the opening distinct between the counter bedside and the bedside in comparison with the third process while making the inside of the opening on the bedside bright in comparison with the inside of the opening on the counter bedside. When, for example, the MRI apparatus include all the lighting units 16-19, only the inside of opening-lateral lighting unit 17, the inside of opening-counter bedside lighting unit 18, and the counter bedside lighting unit 19 are emitted in such an amount that it is not dazzling to the person according to a lighting pattern L9 as an example of the lighting pattern.

Further, when, for example, the MRI apparatus include all the lighting units 16-19, only the inside of opening-lateral lighting unit 17 and the counter bedside lighting unit 19 are emitted in such an amount that it is not dazzling to the person according to a lighting pattern L10 as an example of the lighting pattern.

In the fourth process, the person can be made to have a false feeling that the depth of the opening is shorter than an actual depth by the savanna effect while making only the counter bedside of the opening bright in such a degree that it is not dazzling to the person by making the contrast of the inside of the opening distinct between the counter bedside and the bedside in comparison with the third process while making the inside of the opening on the bedside bright in comparison with the inside of the opening on the counter bedside.

Note that the lighting patterns in the fourth process when the MRI apparatus includes all the lighting units 16-19 are not limited to the lighting patterns L9 and L10.

Here, when an examination is carried out by employing the lighting pattern group in one examination, the lighting pattern is switched during the examination. According to, for example, the lighting pattern group of the foot examination as shown in FIG. 7, the lighting pattern is switched three times. The lighting pattern may be manually switched by operating the input unit 25 during the examination. When, for example, the process in the foot examination shifts from the first process to the second process, the operator depresses a switch of the input unit 25 once so that the lighting pattern is manually switched from a lighting pattern (for example, the lighting pattern L1) suitable for the first process to a lighting pattern (for example, the lighting pattern L2) suitable for the second process.

Further, when, for example, the process in the foot examination shifts from the first process to the second process, the lighting pattern is automatically switched from the lighting pattern suitable for the first process to the lighting pattern suitable for the second process pattern in such a manner that the MRI apparatus recognizes the change of position of the table-top (the up/down and right/left movements of the table-top).

Note that a function for turning off all the lighting units 16-19 may be provided with the input unit 25 so that they can be turned off at once when the person wants to turn off them even if lighting is carried out according to a previously set lighting pattern.

Although the lighting patterns of the respective lighting units 16-19 are explained here using the amount of emitting light as the contents of lighting in FIG. 7, the lighting patterns of the respective lighting units 16-19 may be arranged using the color of emission and the manner of emission as the contents of lighting likewise.

For example, a lighting pattern group composed of lighting patterns in which light is emitted in a warm color in its entirety and a lighting pattern group composed of lighting patterns in which light is emitted in a cold color in its entirety are previously stored to the storage 20 respectively, and the warm color or the cold color is manually selected according to the desire of the operator or the person before the examination. Further, a lighting pattern group composed of lighting patterns in which light is emitted in a warm color in its entirety and a lighting pattern group composed of lighting patterns in which light is emitted in a cold color in its entirety are previously stored to the storage 20 respectively, and the warm color or the cold color is automatically selected based on the patient information of the person, in particular, based on the nationality information before the examination.

Here, the MRI apparatus may be provided with at least one of lighting units 40, 50, and 60 to be explained below in addition to the lighting units 16-19.

Figure 8:
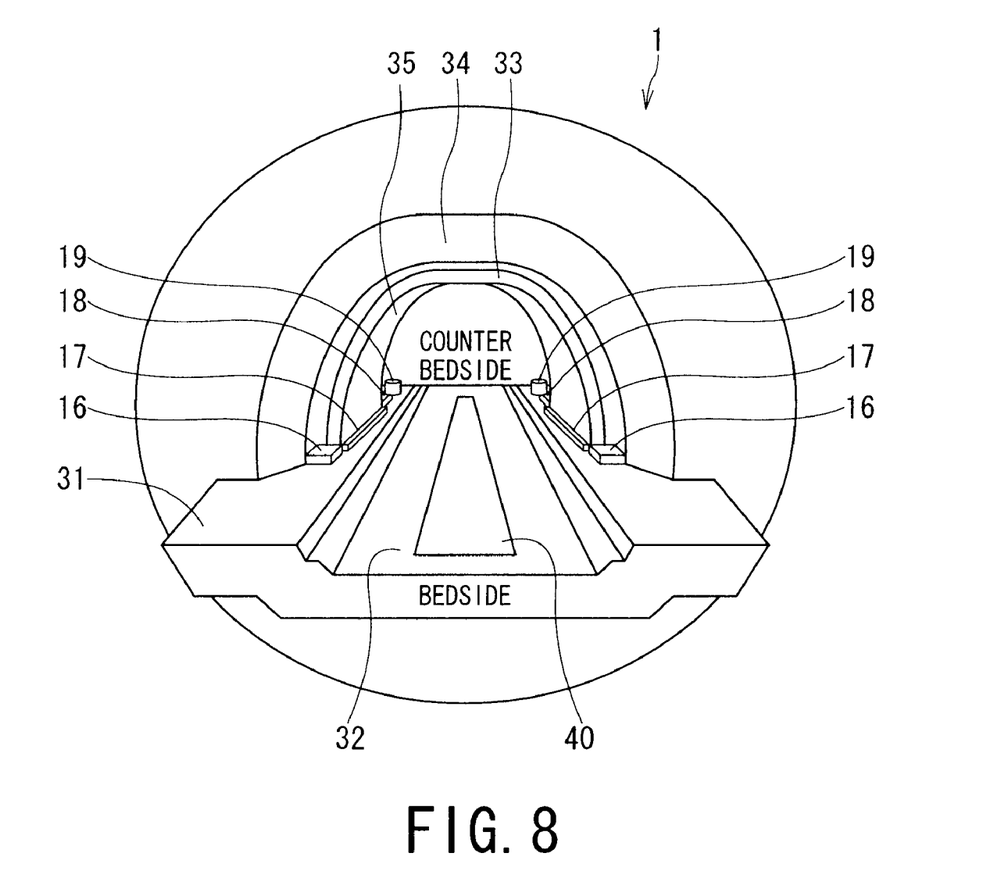
FIG. 8 is a perspective view showing an example of a lighting unit when viewed from a bedside of an opening.

FIG. 8 is a perspective view showing the lighting unit disposed on the support unit 31 of the MRI apparatus of the embodiment when viewed from the bedside of the opening.

As shown in FIG. 8, an on-rail lighting unit 40 as the lighting unit is disposed on the rail 25 of the support unit 31 into which the table-top is inserted. The on-rail lighting unit 40 may be arranged such that a light transmission member is installed along the rail with another second light source with the light source 15 and covered with a transparent or semi-transparent cover so that it is made flat, and light it by transmitting the light from the second light source. Further, a plurality of LEDs may be disposed side by side on the rail 25 and made flat by being covered with a transparent or semi-transparent cover likewise. Note that when the plurality of LEDs are disposed side by side, a manner of emission may be provided with a pattern so that not only they are entirely emitted at a time but also they are partly or sequentially emitted. Note that the cover put on the rail 25 may be provided with a gradation.

When the ceiling portion of the opening is made luminous by the on-rail lighting unit 40, the person has a false feeling that the periphery of the opening is wider that an actual periphery. Further, as the table-top is inserted, the on-rail lighting unit 40 is shielded by the table-top, thereby the opening is made gradually dark. Further, when the table-top is entirely inserted, a power output is suppressed by turning off the on-rail lighting unit 40.

Figure 9:
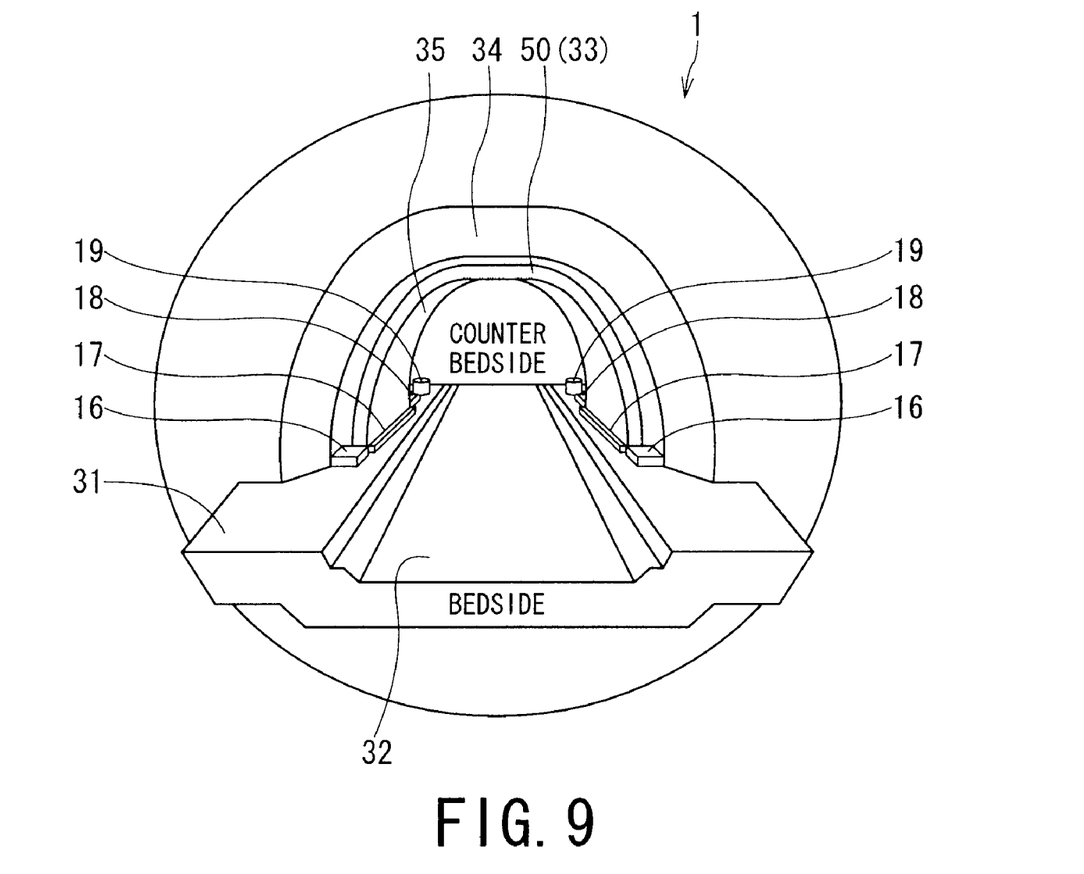
FIG. 9 is a perspective view showing an example of a lighting unit when viewed from a bedside of an opening.

FIG. 9 is a perspective view showing the lighting unit disposed on the taper portion 33 of the cover of the RF coil 5 in the inside of the opening of the MRI apparatus of the embodiment when viewed from the bedside of the opening.

As shown in FIG. 9, a taper portion lighting unit 50 as the lighting unit is disposed on the taper portion 33 of the cover of the RF coil 5 installed in the opening. The taper portion lighting unit 50 may be arranged such that a light transmission member is installed along the taper portion 33 with another third light source with the light source 15, and light it by transmitting the light from the third light source. Specifically, the taper portion lighting unit 50 may be arranged such that a plurality of LEDs are disposed on the taper portion 33 side by side. Note that when the plurality of LEDs are disposed side by side, a manner of emission may be provided with a pattern so that not only they are entirely emitted at a time but also they are partly or sequentially emitted.

The taper portion lighting unit 50 is emitted as well as the inside of opening-counter bedside lighting unit 18 and the counter bedside lighting unit 19 are emitted. The taper portion lighting unit 50 may be provided with a gradation so that it is made brighter as it is nearer to the support unit 31 and is made darker as it is farther therefrom. Further, when the taper portion lighting unit 50 has the plurality of LED lamps, it may be provided with a pattern so that the LED lamps are emitted individually.

Further, when the counter bedside lighting unit 19 is combined with the taper portion lighting unit 50, the shade S caused by the step of the cover of the RF coil 5 can be prevented, thereby a feeling of siege to the opening caused by the shade S can be reduced.

Figure 10:
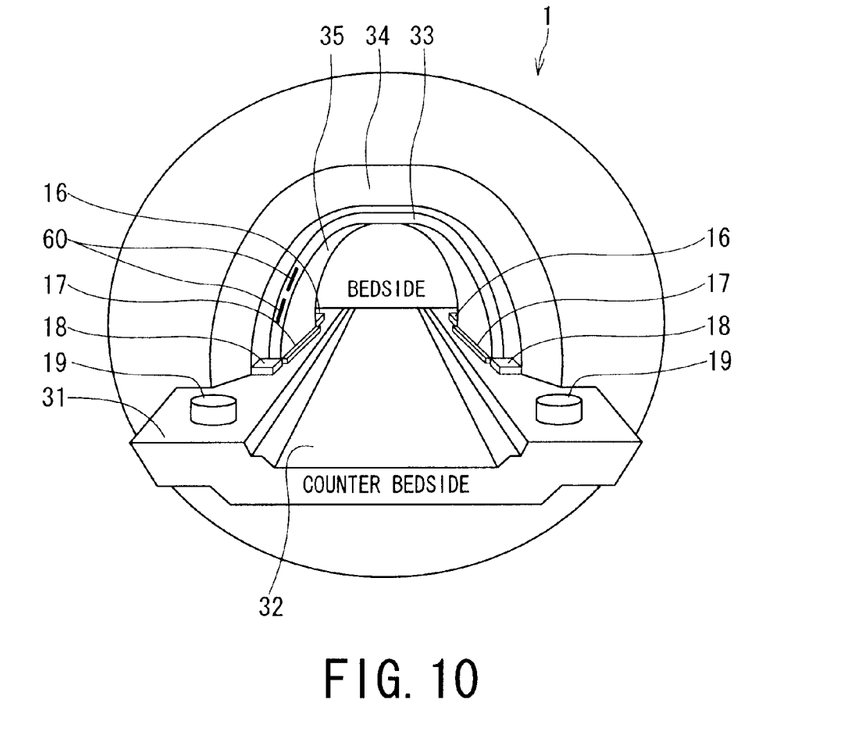
FIG. 10 is a perspective view showing an example of a lighting unit when viewed from a counter bedside of an opening.

FIG. 10 is a perspective view of the remaining time display lighting unit disposed at a part of the wall in the opening of the MRI apparatus of the embodiment when viewed from the counter bedside of the opening.

As shown in FIG. 10, a remaining time display lighting unit 60 as the lighting unit for displaying a remaining time using lighting unit is disposed at the opening, for example, on the wall by which the opening is formed. The remaining time display lighting unit 60 is formed in a slender bar shape, and the remaining time is displayed by increasing or decreasing the amount of emitting light of the bar. Otherwise, the remaining time may be displayed by changing several colors.

The person is notified of the remaining time of the examination by the light emitted from the remaining time display lighting unit 60. The remaining time display lighting unit 60 displays the remaining time by increasing or decreasing the length of the light bar, that is, by increasing or decreasing the amount of emitting light in the bar, and the person can confirm the remaining time by confirming the amount of emitting light. Further, the person may confirm the remaining time by the change of several colors.

Note that the lighting units 40, 50, and 60 may be emitted in association with the lighting patterns of the lighting units 16-19.

In the MRI apparatus of the embodiment, a cover may be put on at least one of the respective lighting units 16-19, 40, 50, and 60 to change the color of the light, and the cover may be optionally removed and replaced with other cover. In this case, the color of lighting can be simply changed to a color which the person wants in each examination.

Further, in the MRI apparatus of the embodiment, the respective lighting units 16-19, 40, 50, and 60 may be turned off or the amount of emitting light may be suppressed to prevent the person from feeling dazzling during the examination. In this case, the person can be subjected to the examination in a settled state.

Further, since the MRI apparatus of the embodiment can change the amount of emitting light of the lighting units and the pattern of the manner of emission by a simple operation and thus a state of lighting can be changed at once according to the desire of the person, the person can be prevented from being applied with an uncomfortable feeling and a feeling of uneasiness.

Note that although the plurality of specific examples according to the present invention are exemplified in the embodiment, the present invention can include various embodiments by combining the colors of emission, the amounts of emitting light and the manners of emission of the respective lighting units 16-19, 40, 50, and 60 in addition to the above embodiment.

What is claimed is:

1. An MRI apparatus, comprising:
    a gantry accommodating a static field magnet configured to generate a static field, a gradient coil configured to generate a gradient magnetic field, and an RF coil configured to transmit or receive an RF pulse, the gantry having an opening into which a person is inserted;
    a bed having a removable table-top for use inside and outside of the opening; and
    a plurality of lighting units configured to light the gantry such that a light intensity at a counter bedside side of the gantry opposite to a bedside side of the gantry across the opening is higher than a light intensity at the bedside.

2. An MRI apparatus according to claim 1, wherein the plurality of lighting units are disposed on a support unit, supporting the table-top, in one straight line from the bedside to the counter bedside.

3. An MRI apparatus according to claim 1, wherein a lighting unit of the plurality of lighting units is disposed at an inside position of the opening at a lower half portion of the opening.

4. An MRI apparatus according to claim 1, wherein at least one of the lighting units lights up a shadow formed by a step made by a cover of the RF coil.

5. An MRI apparatus according to claim 1, further comprising a taper portion lighting unit disposed at a position of a taper portion made by a cover of the RF coil.

6. An MRI apparatus according to claim 1, further comprising:
    a lighting pattern group setting unit configured to set a lighting pattern group in respective examination made by combining lighting patterns set in the respective lighting units with respective processes in the examination; and
    a storage storing the lighting pattern group, wherein the lighting pattern group is chosen before the examination, and lighting is carried out according to the chosen lighting pattern equivalent to the process during the examination.

7. An MRI apparatus according to claim 6, wherein each lighting pattern includes at least one of an amount of light and a manner of light set in the respective lighting unit.

8. An MRI apparatus according to claim 6, further comprising:
    an input unit configured to change a lighting pattern manually in the respective process.

9. An MRI apparatus according to claim 1, wherein at least one of the plurality of lighting units is an LED lamp configured to emit three colors.

10. An MRI apparatus according to claim 9, further comprising:
    a lighting pattern group setting unit configured to set a lighting pattern group made by combining lighting patterns set in the respective lighting units with respective processes in the examination; and
    a storage storing the lighting pattern group, wherein the lighting pattern group is chosen before the examination, and lighting is carried out according to the chosen lighting pattern equivalent to the process during the examination.

11. An MRI apparatus according to claim 10, wherein each lighting pattern includes at least one of a color of emission, an amount of emitting light, and a manner of emission set in the respective lighting unit.

12. An MRI apparatus according to claim 10, further comprising:
    an input unit configured to change a lighting pattern manually in the respective process.

13. An MRI apparatus according to claim 10, wherein the lighting pattern group is selected based on patient information of the person.

14. An MRI apparatus, comprising:
    a gantry accommodating a static field magnet configured to generate a static field, a gradient coil configured to generate a gradient magnetic field, and an RF coil configured to transmit or receive an RF pulse, the gantry having an opening into which a person is inserted;
    a bed having a removable table-top for use inside and outside of the opening; and
    a lighting unit disposed at an inside position of the opening on a bedside of the gantry, the lighting unit configured to light a step in an inside of the opening on the bedside or a cover of the RF coil that rises into the opening.

15. An MRI apparatus, comprising:
    a gantry accommodating a static field magnet configured to generate a static field, a gradient coil configured to generate a gradient magnetic field, and an RF coil configured to transmit or receive an RF pulse, the gantry having an opening into which a person is inserted;
    a bed having a removable table-top for use inside and outside of the opening; and
    a photoconductor disposed along a side in the opening, the photoconductor configured to transmit light from a light source.

16. An MRI apparatus, comprising:
    a gantry accommodating a static field magnet configured to generate a static field, a gradient coil configured to generate a gradient magnetic field, and an RF configured to for transmit or receive an RF pulse, the gantry having an opening into which a person is inserted;
    a bed having a removable table-top for use inside and outside of the opening;
    a first lighting unit disposed at one of a bedside of the gantry and a counter bedside of the gantry opposite to the bedside across the opening, the first lighting unit configured to light the inside of the opening; and
    a second lighting unit disposed at the other of the bedside and the counter bedside, the second lighting unit configured to light a shade formed by a step of the opening by the lighting from the first lighting unit.

17. An MRI apparatus according to claim 16, wherein an amount of light about the first lighting unit is larger than an amount of light about the second lighting unit.

* * * * *